United States Patent
Cappelaere et al.

(10) Patent No.: US 9,764,151 B2
(45) Date of Patent: Sep. 19, 2017

(54) NEURAL NETWORK SYSTEM FOR THE EVALUATION AND THE ADAPTATION OF ANTITACHYCARDIA THERAPY BY AN IMPLANTABLE DEFIBRILLATOR

(71) Applicant: SORIN CRM SAS, Clamart (FR)

(72) Inventors: Charles-Henri Cappelaere, Paris (FR); Amel Amblard, Sceaux (FR); Sylvain Christophle-Boulard, Sainte Geneviève des Bois (FR); Gérard Dreyfus, Gif sur Yvette (FR); Rémi Dubois, Mérignac (FR); Pierre Roussel, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/598,025

(22) Filed: Jan. 15, 2015

(65) Prior Publication Data
US 2015/0196770 A1    Jul. 16, 2015

(30) Foreign Application Priority Data
Jan. 16, 2014  (FR) .................................. 14 50357

(51) Int. Cl.
*A61N 1/39* (2006.01)
*G06N 3/02* (2006.01)

(52) U.S. Cl.
CPC ......... *A61N 1/3925* (2013.01); *A61N 1/3937* (2013.01); *A61N 1/3956* (2013.01); *A61N 1/3987* (2013.01); *G06N 3/02* (2013.01)

(58) Field of Classification Search
CPC .. A61N 1/362; A61N 1/3621; A61N 1/36585; A61N 1/3925; A61N 1/39; A61N 1/3937; A61N 1/3956; A61N 1/3962
See application file for complete search history.

(56) References Cited

U.S. PATENT DOCUMENTS 5,251,626 A * 10/1993 Nickolls ............ A61N 1/36514
                                                         128/925
5,280,792 A    1/1994 Leong et al.
(Continued)

FOREIGN PATENT DOCUMENTS

DE          43 37 110      11/1994
WO    WO-2009/088627      7/2009

OTHER PUBLICATIONS

Preliminary Search Report for French Patent Application No. FR 1450357, dated Aug. 21, 2014, 1 page.

*Primary Examiner* — George Evanisko
(74) *Attorney, Agent, or Firm* — Foley & Lardner LLP

(57) ABSTRACT

The system includes an active medical device with means for delivering defibrillation shocks; means for continuous collection of the patient current cardiac activity parameters; and evaluator means with neuronal analysis comprising a neural network with at least two layers. This neural network comprises upstream three neural sub-networks receiving the respective parameters divided into separate sub-groups corresponding to classes of arrhythmogenic factors; and downstream an output neuron coupled to the three sub-networks and capable of outputting an index of risk of ventricular arrhythmia. The risk index is compared with a given threshold, to enable or disable at least one function of the device in case of crossing of the threshold.

18 Claims, 3 Drawing Sheets

(56) References Cited

U.S. PATENT DOCUMENTS

| | | | |
|---|---|---|---|
| 6,192,273 B1* | 2/2001 | Igel | A61B 5/0464 |
| | | | 600/518 |
| 6,263,238 B1* | 7/2001 | Brewer | A61N 1/3925 |
| | | | 607/5 |
| 7,657,313 B2 | 2/2010 | Rom | |
| 2003/0097153 A1 | 5/2003 | Bardy et al. | |
| 2008/0147130 A1 | 6/2008 | Rom | |
| 2009/0281441 A1* | 11/2009 | Zhang | A61B 5/0468 |
| | | | 600/516 |
| 2011/0190650 A1 | 8/2011 | McNair | |
| 2011/0301479 A1* | 12/2011 | Ghanem | A61B 5/04012 |
| | | | 600/515 |
| 2013/0123869 A1 | 5/2013 | Rom | |

\* cited by examiner

NEURAL NETWORK SYSTEM FOR THE EVALUATION AND THE ADAPTATION OF ANTITACHYCARDIA THERAPY BY AN IMPLANTABLE DEFIBRILLATOR

CROSS REFERENCE TO RELATED APPLICATIONS

This application claims the benefit of and priority to French Patent Application No. 1450357, filed Jan. 16, 2014, which is hereby incorporated by reference herein in its entirety.

BACKGROUND

The invention relates to "active implantable medical devices" as defined by the Directive 90/385/EEC of 20 Jun. 1990 of the Council of the European Communities, specifically implantable cardioverter defibrillators (ICDs), which are devices capable of applying an antitachycardia therapy by delivering defibrillation or cardioversion shocks, that is to say electric pulses of high energy, considerably exceeding the energy delivered by a myocardium stimulation.

These devices are generally implanted for primary prevention in patients with a particular clinical problem, typically patients who have had a heart attack with electrophysiological abnormalities, or coronary and/or heart failure patients with reduced ejection fraction. Specifically, the current recommendations for an indication of prophylactic implantation of a defibrillator are:

Patient with a coronary artery disease, without or with mild to moderate symptoms of heart failure and ejection fraction ≤30% measured at least one month after a heart attack, or Patient with apparently primitive dilated cardiomyopathy, with ejection fraction ≤35% and symptoms of mild to moderate heart failure (NYHA class II or III).

However, when examining afterwards the effective utilization rate (delivery of at least one therapy) of defibrillators that were implanted in patients using these criteria, it is shown that very few patients benefit from their defibrillator. In a 2005 study, it appears that 81% of patients have never been subjected to a defibrillator therapy over a period of 5 years.

The implantation of a defibrillator is not a trivial operation. Firstly, the defibrillator algorithms may wrongly detect ventricular tachycardia, leading to the delivery of unnecessary or deleterious shocks, affecting the quality of life of the patient. Beyond the inconvenience caused by this type of painful and distressing shock for the patient, it was also demonstrated that these inappropriate shocks increase the risk of death. Secondly, the defibrillation leads are fragile and complex devices, with a significantly higher failure rate than that of simple pacing leads. Patients implanted with an implantable defibrillator are therefore statistically more often the subject of reoperation than those with a simple pacemaker or resynchronizer. Thirdly, implanted defibrillators for primary prevention are often programmed to treat only the very high rate arrhythmias. In the area of "slow ventricular tachycardia" ("slow TV"), between 100 and 150 bpm, all therapies are disabled, this area being only used for monitoring the patient. However, the slow TV can be halted by alternative therapies to shock delivery, including therapies called "ATP" (AntiTachycardia Pacing) acting through a programmed stimulation at a frequency adapted for tachycardia, which would prevent the patient from worsening conditions.

One object of the invention is to overcome these difficulties by proposing a system for the evaluation and adaptation of antitachycardia therapy by shock delivery. This system includes an implantable defibrillator that can automatically evaluate the actual risks of deleterious ventricular arrhythmia in the patient, and automatically adapt its programming (modification of rhythm analysis algorithms, of the detection sensitivity, etc.) according to risk actually incurred by the patient, so as not to trigger an alarm and/or activate a potential shock therapy in the event of major arrhythmia risk. Otherwise, the shock therapy can be deactivated, thereby avoiding the delivery of inappropriate, painful, and harmful shocks, favoring a potential ATP therapy.

Most analysis techniques proposed so far to quantify the risk of developing malignant ventricular arrhythmia are based on the study of a single descriptor (univariate study): case of Non-Sustained Ventricular Tachycardia (NSVT), Heart Rate Variability (HRV), Heart Rate Turbulence (HRT), QRS width, QT length, etc.

For example, US 2011/0190650 A1 assesses the risk of sudden death based solely on the dispersion of the QT segment, a descriptor measured on ECG recordings and compared to a preset value. If the measured dispersion is significantly different from the preset value, the patient is considered at risk of sudden death, which justifies the prophylactic implantation of a defibrillator.

Multivariate studies were also conducted, for example to assess the T Wave Alternans combination (TWA)+late potentials, or the combination HRT+TWA+reduced ejection fraction. These multivariate studies, however, only evaluate linear combinations of descriptors, with specificity only slightly higher than what could be obtained with the other techniques.

WO 2009/088627 A1 is thus based on the comparison of descriptors obtained from Holter monitoring with predetermined values, the risk criterion being based on the number of descriptors beyond pre-established thresholds.

US 2011/0301479 A1 discloses calculating all Holter recording descriptors and dividing them into three categories, corresponding to the decomposition of the Coumel triangle (which will be explained below). In each of these three categories, the descriptors are compared to preset values considered "normal", and for each category, a risk sub-criterion is established based on the ratio of the descriptors which are within the bounds of this "normality" and those who are outside these bounds. The final criterion of risk of sudden cardiac death is the ratio between the number of these three, validated or not, categorical risk sub-criteria.

U.S. Pat. No. 5,251,626 A describes a device for detection and treatment of arrhythmias implementing a neural network. This technique however has the drawback of making overall analysis of the various parameters used to trigger an arrhythmia, by averaging and mixing information from the various relevant arrhythmogenic criteria. The specificity of the device is thus relatively low, leading to a high proportion of false positives and false negatives.

These different techniques above are thus in practice not very discriminatory because they rely on too simple models (with single descriptor and/or based on threshold crossings) and do not reflect the reality of physiological phenomena, which involve a number of important nonlinearly interacting factors.

SUMMARY

Certain embodiments of the present invention provide a system including an active implantable medical device that includes methods for delivering defibrillation shocks, methods for continuously collecting current cardiac activity parameters of the patient, and evaluator methods including a neural network with at least two layers. The system may be similar to that described in U.S. Pat. No. 5,251,626 A above.

According to certain preferred embodiments, a neural network includes, upstream, three neural sub-networks, receiving the parameters divided into three distinct respective subgroups corresponding to classes of arrhythmogenic factors. One of said sub-groups may include electrophysiological substrate descriptors, a second one of sub-groups may include pejorative modulator descriptors, and a third of said sub-groups may include trigger factor descriptors. A neural network may also include, downstream, a neural network including at least one output neuron output coupled to the three upstream sub-networks and able to deliver an indication of risk of ventricular arrhythmia. The active medical device may further include methods adapted to compare the index of risk of ventricular arrhythmia to a given threshold and to activate or disable at least one function of the device in case of threshold crossing.

The on or off function of the device, when crossing said threshold, may in particular be a function of the group including: production of an alarm; activation/deactivation defibrillation shock therapies; activation/deactivation of new therapy zones; modification of the sensitivity of the arrhythmia detector; activation/deactivation of algorithms; and/or modification of therapy parameters.

For its implementation, the above system may further include a database of reference patients, storing for each reference patient: a plurality of descriptors developed based on parameters of cardiac activity collected for the reference patient, and a marker indicating the proven or not occurrence of ventricular arrhythmia for the reference patient. The system may also include methods adapted to define the structure of the neural network with supervised learning from the database of reference patients, including for each of the subgroups corresponding to classes of arrhythmogenic factors: methods for selection of the most relevant descriptors; methods for determination of the structure of the neural sub-networks; and methods for optimization of the neural sub-networks. The system may also include methods for building the neural network, and learning methods of the neural network.

The first subgroup may include descriptors of electrophysiological substrate selected from the group comprising: QRS residuum and/or T-wave residuum; QRS-T angle; $QT_{apex}$ intervals and/or $QT_{end}$; T wave downslope; and/or ST segment offset. The second subgroup may include pejorative modulator descriptors selected from the group including: heart rate turbulence; variability index between successive complexes; standard deviation of the normal intervals; and/or the Poincaré representation of heart rate variability. The third subgroup may include trigger factor descriptors selected from the group comprising: ventricular bigeminy or trigeminy episode; ventricular tachycardia; and/or supraventricular premature contraction.

DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the invention will now be described. Regarding its software aspects, the invention may be implemented by appropriate programming of the controlling software of a known stimulator, for example a cardiac pacemaker, resynchronizer or defibrillator, including methods of acquisition of a signal provided by endocardial leads. The invention may notably be applied to implantable devices, such as that of the Paradym family, manufactured and commercialized by Sorin CRM, Clamart, France.

These devices include programmable microprocessor circuitry to receive, format and process electrical signals collected by implantable electrodes, and deliver stimulation pulses to these electrodes. It is possible to download, by telemetry, software that is stored in memory and executed to implement the functions of the invention that are described below.

The invention is primarily implemented by software and appropriate algorithms executed by a microcontroller or a digital signal processor. For the sake of clarity, the various processing applied will be broken down and diagrammed by a number of different functional blocks in the form of interconnected circuits, however this representation is only illustrative. These circuits incorporate common elements and in practice correspond to a plurality of functions performed by a single overall software.

Figure 1:
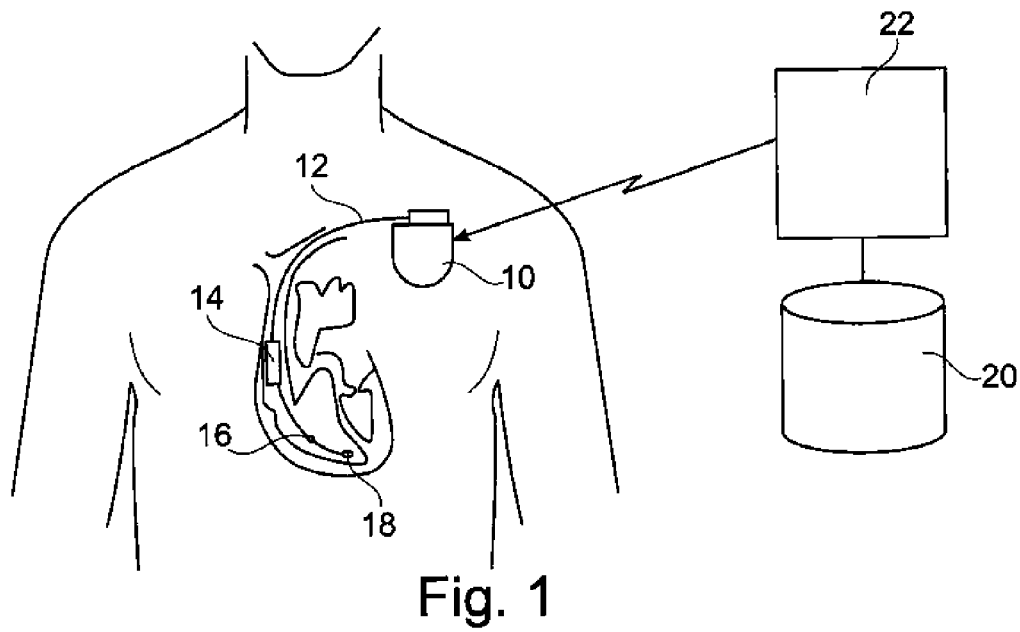
FIG. 1 schematically shows the different elements involved in the implementation of the invention, with an implantable defibrillator in a patient.

In FIG. 1, numeral reference 10 denotes a cardiac implant such as a defibrillator or a pacemaker/defibrillator, provided with a lead 12 provided with a coil 14 forming a defibrillation electrode, and a plurality of electrodes or sensors 16, 18, allowing the collection of various cardiac activity signals such as endocardial electrograms (EGM) and endocardial acceleration signal (EA) in particular. The device 10 may also be provided with various methods for sensing signals reflecting the metabolic activity of the patient (intracardiac and/or transpulmonary bio-impedance, minute ventilation, etc.) or patient physical activity (acceleration sensor). These various signals will hereafter collectively be referred to with the term "cardiac activity parameters."

The system also includes a reference patients database 20 for storing, for a patient population that has been previously tracked, information derived from various parameters of heart activity collected for each patient and for each of them, a label or marker indicating that a malignant ventricular arrhythmia is or is not detected for a predetermined monitoring period.

This database is used by a module 22 to determine the optimal structure for the studied problem, of an automatic classifier and to perform supervised learning of said classifier, the latter including, according to the invention, a neural network. The model thus designed is programmed in the implanted device 10 so that it can continuously evaluate, by methods of the classifier, the risk of arrhythmia of the implanted patient.

Figure 2:
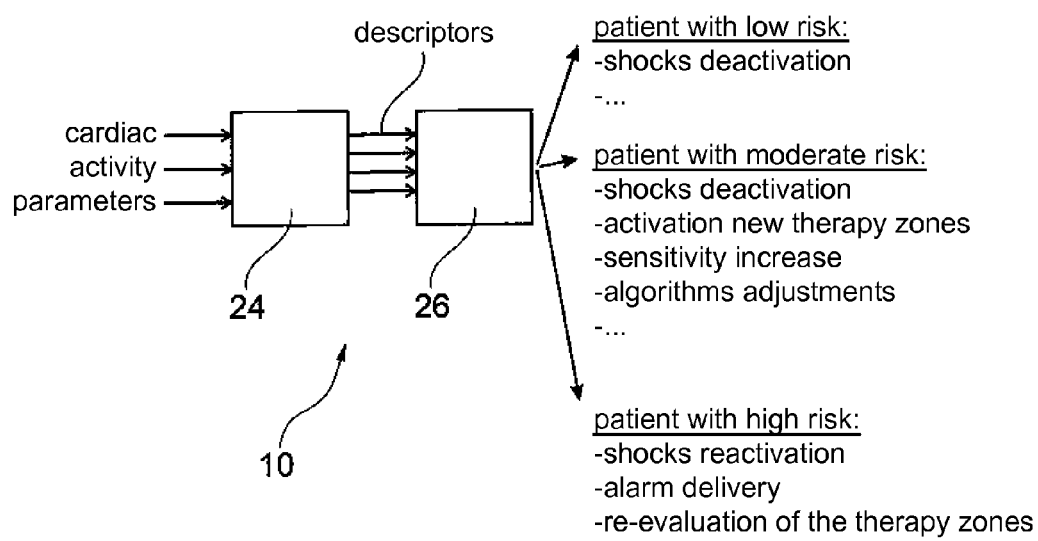
FIG. 2 schematically illustrates the operation of the arrhythmia risk assessor implemented within the implantable defibrillator.

FIG. 2 schematically illustrates the principle of operation of this arrhythmia risk assessor as implemented within the implantable device 10. The various parameters of cardiac activity collected by the implantable device are initially subjected to a first processing (block 24) to extract a number of "descriptors". These descriptors are data calculated from the parameters of cardiac activity, relevant for the assessment of risk of arrhythmia. Various examples of such descriptors are presented below.

These descriptors are input to an arrhythmia risk estimation module (block 26), which includes methods for obtaining at the output, from the plurality of descriptors inputted, a single index that quantifies, for the implanted patient, the current risk of malignant ventricular arrhythmia. The index thus obtained is compared with a predetermined threshold, the patient being then referred to as "low risk" or "high risk" patient as appropriate.

The threshold crossing in one direction or the other, has the effect of changing one or more functions of the device. For example, for a patient becoming a "high risk" patient: alarm emission; activation or reactivation of defibrillation shock therapies. In another example, for a patient becoming a "moderate risk" patient: disabling of defibrillation shock therapies; activation of new therapy zones, so as to not only treat high rate arrhythmias, but also the "slow ventricular tachycardias" with a rhythm between 100 and 150 bpm; increased arrhythmia detector sensitivity, for example a threshold of detected wave amplitude set to 0.4 mV; disabling of certain algorithms; and/or adjusting of parameters of the therapy. In yet another example, for a patient becoming a "low risk" patient: disabling of defibrillation shock therapies, to reduce the risk of inappropriate, deleterious shocks, activating only in the ATP-type therapies; lowering of the arrhythmia detector sensitivity; activation/deactivation of certain algorithms, etc.

The descriptors that may be used to assess the arrhythmia risk index are divided into three groups. The breakdown into three groups allows for a mathematical transcription of a physiological approach to the problem, schematized by the "Coumel triangle." To develop and maintain an arrhythmia requires the coexistence of three factors, namely: (1) structural or functional pathologic field ("Electrophysiological substrate" top of the triangle) such as a myocardium slow conduction zone, stroke, history, a disease of the electrophysiological characteristics of the cells, etc.; (2) a triggering event ("trigger factor" top of the triangle): increase in heart rate, extrasystole, etc.; and (3) an environment that favors the perpetuation of this arrhythmia ("pejorative modulators" top of the triangle): decreased heart rate variability, hypokalemia, etc.

In the present case, the choice of the group to which each descriptor is assigned is motivated by the nature of the physiological phenomenon for which this parameter is relevant. The "electrophysiological substrate" descriptor group may include (but not exhaustive or limited to):

Residuum QRS and residuum T-Wave markers, which are, respectively, markers of the heterogeneity of ventricular depolarizations and repolarizations. These descriptors can be obtained by a principal component analysis of signals corresponding to QRS on the one hand, and to the T wave, on the other hand;

The QRS-T angle, i.e. the angle between the axis of the ventricular depolarization and that of the ventricular repolarization. These axis are computed with a Principal Component Analysis of an EGM signal;

The $QT_{apex}$ and $QT_{end}$ intervals, which are, respectively, the intervals from the beginning of the QRS complex and the top or the end of the T wave. These intervals are measured from an EGM signal recording and may be the subject of a correction based on the instantaneous heart rate;

The downward slope of the T wave, corresponding to the director coefficient of the steepest linear regressions on three consecutive points from the top of the T wave; and The ST segment shifting, measured at the "J" point (60 ms after the end of the QRS), with respect to the isoelectric line.

The "trigger factors" group of descriptors may include the occurrence of episodes such as (but not exhaustive or limited to):

Ventricular bigeminy or trigeminy;
Ventricular tachycardia;
Supraventricular extrasystole; and
Supraventricular doublet.

The "pejorative modulators" group of descriptors may include (but not exhaustive or limited to):

Heart rate turbulence (HRT), characterized by the Turbulence Onset (TO) and Turbulence Slope (TS) values;

The variability index, defined as the percentage of mean differences between two successive QRS;

The SDANN value (Standard Deviation of Averages of All Normal-to-Normal Intervals, standard deviation of the averages of all normal-normal intervals);

The "Poincare Plot SD2", which is a two-dimensional representation of the RR intervals as a function of the preceding RR intervals, approximated by an ellipse the major axis and the minor axis of which are two representative descriptors.

Figure 3:
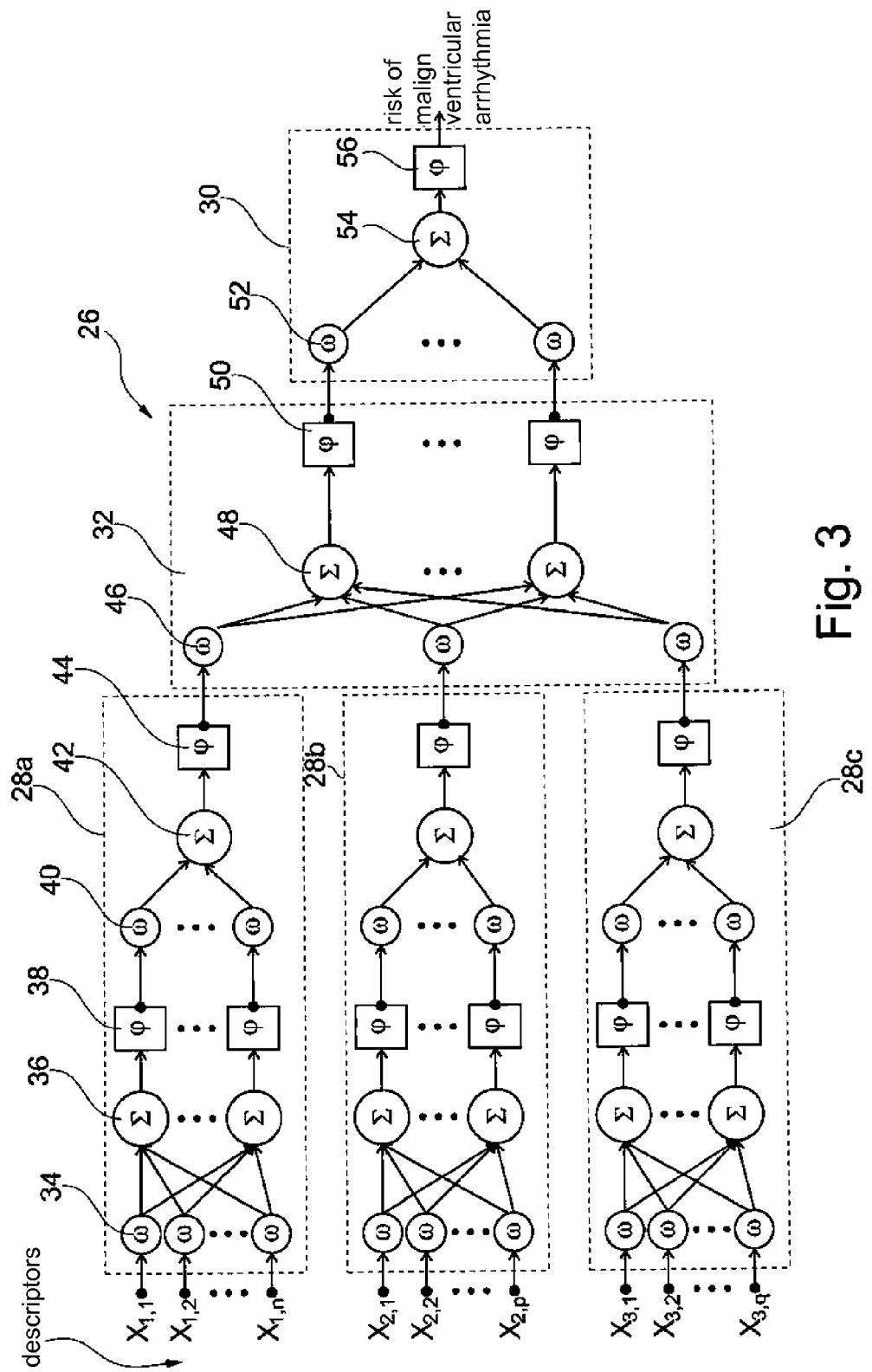
FIG. 3 is an example of a neural network suitable for implementation of the arrhythmia risk assessor according to the invention.

FIG. 3 illustrates an exemplary neural network 26 receiving as input the descriptors described above, and outputting a representative index of the risk of malignant ventricular arrhythmia. The network 26 includes three upstream separate sub-networks 28a, 28b and 28c receiving the respective descriptors corresponding to each of the three groups described above (electrophysiological substrate, trigger factor and pejorative modulators), these three sub-networks being connected, downstream side, to an output neuron 30 outputting the index representative of the risk of ventricular arrhythmia. In the example shown, the upstream networks 28a, 28b and 28c are connected to the output neuron 30 via a hidden layer 32, however this example is not limiting and the sub-networks 28a, 28b, 28c may be directly connected to the output neuron 30.

The representation of FIG. 3 is the canonical representation of a neural network according to one embodiment of the invention. At 34 the different weights co respectively are applied to each of the inputs (descriptors) $X_{1,1} \ldots X_{1,n}$ of the sub-network 28a, to each of the inputs $X_{2,1} \ldots X_{2,p}$ of the second sub-network 28b, and to each of the inputs $X_{3,1} \ldots X_{3,q}$ of the third sub-network 28c.

The hidden neurons in each sub-network 28a, 28b, 28c perform a weighted summation at 36 of the different inputs and then apply at 38 a function $\phi$ of activation of the hidden neurons. The resulting outputs are weighted at 40 and are subjected at 42 to a summation and at 44 of the activation function of the output of the sub-network.

Each of the respective outputs of the sub-networks 28a, 28b, 28c is subject, at 46, to a weighting by a weight co for summation at 48 and application of activation function 50 of the hidden neurons of the hidden layer 32. The outputs of this hidden layer are themselves subject to a weighting at 52 by respective weights co for the output neuron 30, which sums at 54, and the application of the final activation function at 56.

In a simplified configuration each of the sub-networks 28a, 28b, 28c may, however, be composed of a single neuron, with the output of each sub-network 28a, 28b, 28c connected to the output neuron 30, without hidden layer or hidden neurons.

Figure 4:
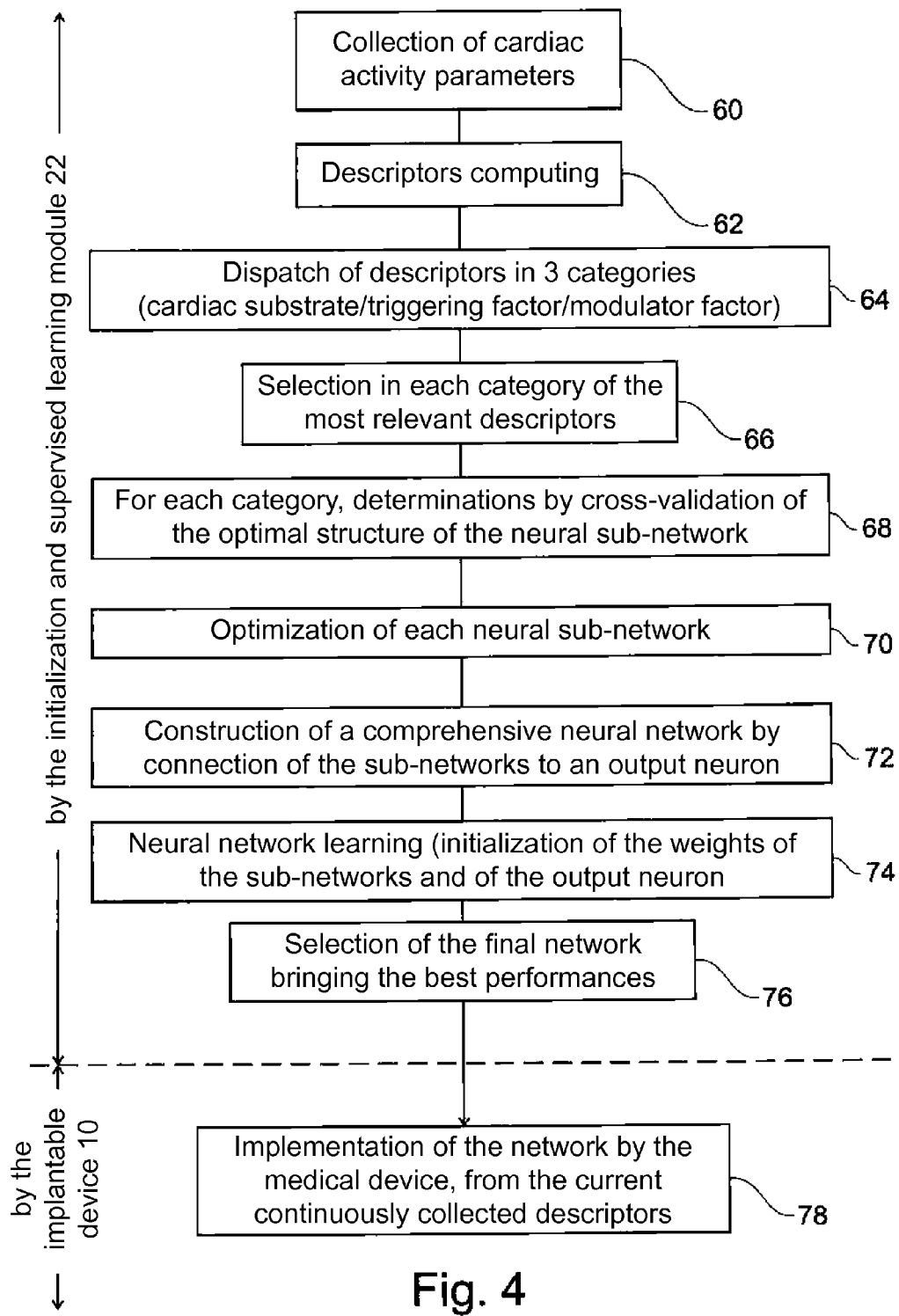
FIG. 4 is a flow chart explaining the steps of the construction and of the learning of the neural network used for implementation of the invention.

FIG. 4 is a flow chart explaining the different stages of construction and learning of the neural network as described above. The parameters of cardiac activity are collected for a reference patient population (step 60) and the corresponding descriptors are calculated and stored in the database 20 (step 62).

These reference patients are implanted with a defibrillator for primary prevention, and are monitored over a long period of time, typically at least six months. The database is labeled, that is to say, it is known for each patient whether or not he/she underwent therapy with at least one defibrillation shock delivered by the implant, during the considered period. The descriptors that were calculated are allocated (step 64) into three categories corresponding to the three arrhythmogenic factors causing arrhythmia (electrophysiological substrate, trigger factor and pejorative modulators) as indicated by the principle of the Coumel triangle. This division into three groups of descriptors translates physiological knowledge and, on the other hand, limits the complexity of the final network neurons.

The next step (step 66) is a selection in each category of the most relevant descriptors, for example by processing such as Gram-Schmidt orthogonalization with probe vector, which can classify in each category the descriptors based on their ability to "explain" the label of the patients, that is to say whether or not an appropriate therapy in the period exists. This possibly eliminates one or more descriptors that would not be relevant or not relevant enough for the purpose.

For each descriptor class, the optimal structure of the neural network (that is to say, each of the sub-networks 28a, 28b, 28c of FIG. 3) receiving as input the descriptors of the given class is determined by cross validation using a technique known per se (step 68). This structure determination of the sub-networks 28a, 28b, 28c has the purpose of determining the number of hidden neurons, so that the network is able to reproduce what is deterministic in the data applied to it. Note that the decomposition of descriptors into three different subgroups allows, for the same number of input neurons, to greatly reduce the number of parameters to be adjusted to determine the network architecture.

The different sub-networks are then optimized (step 70) and then connected to an output neuron (the neuron 30 in FIG. 3) with or without intermediate hidden layer (step 72). The final network thus formed is subject to multiple learning (step 74) by setting the weight co of the three sub-networks 28a, 28b, 28c according to the network previously determined, and by randomly setting the weights ω of the output neuron (step 74). The final network providing the best performance is then selected (step 76), and it can be programmed in the control software of the implantable device 10.

The network is then, continuously, implemented by the device 10 as explained above with reference to FIG. 2, from the current descriptors calculated from the various parameters of heart activity collected from the patient carrying the device 10 (step 78).

Moreover, the network can be updated regularly. This update can be done using a computer, a tablet, an event recorder such as the SpiderFlash model produced and marketed by Sorin CRM, Clamart, France, which can be synchronized with the implant for the update.

The invention claimed is:

1. A system for evaluation and adaptation of an antitachycardia therapy, comprising:
at least one lead; and
an active medical device adapted to be implanted in a patient, the active medical device performs at least one function and comprises a neural network with at least two layers and configured to:
deliver defibrillation shocks via the lead;
collect parameters relating to cardiac activity of the patient;
extract three subgroups of descriptors from the collected parameters, wherein the three subgroups of descriptors correspond to classes of arrhythmogenic factors, a first one of the subgroups comprising electrophysiological substrate descriptors, a second one of the subgroups comprising pejorative modulator descriptors, and a third one of the subgroups comprising trigger factor descriptors;
for each of the three subgroups of descriptors, classifying each descriptor based on an ability of the descriptor to label the patient and selecting a descriptor for each of the three subgroups of descriptors having a classification indicating the descriptor is relevant to the patient;
evaluate the selected descriptors using the neural network with at least two layers, the at least two layers comprising:
three neural sub-networks, each configured to process a different one of the selected descriptors, wherein each neural sub-network generates an output; and
at least one output neuron coupled to the three neural sub-networks and configured to generate an index of risk of ventricular arrhythmia based on the output of at least one of the three neural sub-networks; and
compare the index of risk of ventricular arrhythmia to a threshold and activate or disable the at least one function of the active medical device in response to the index crossing the threshold.

2. The system of claim 1, wherein the function activated or disabled in response to the index crossing the threshold is at least one of:
producing an alarm;
activating or deactivating defibrillation shock therapies;
activating new therapy zones;
adjusting a sensitivity of an arrhythmia detector;
activating or deactivating one or more algorithms; or
modifying one or more therapy settings.

3. The system of claim 1, further comprising:
a database of reference patients, storing for each reference patient:
a plurality of descriptors developed from the parameters relating to the cardiac activity collected for the reference patient; and
a marker indicating whether a ventricular arrhythmia was detected in the reference patient;
wherein the active medical device is further configured to define a structure of the neural network by learning from the database of reference patients, wherein the active medical device is configured to, for each of the subgroups corresponding to arrhythmogenic factor classes:
   determine the structure of the neural sub-networks; and
   optimize the neural sub-network.

4. The system of claim 3, wherein the first one of the subgroups comprises electrophysiological substrate descriptors selected from a group comprising:
   a QRS residuum;
   a T-Wave residuum;
   a QRS-T angle;
   QTapex intervals;
   QTend intervals;
   a downslope of a T wave; or
   a ST segment elevation.

5. The system of claim 3, wherein the second one of the subgroups comprises pejorative modulator descriptors selected from a group comprising:
   a heart rate turbulence;
   a variability index between successive complexes;
   a standard deviation of normal range averages; or
   a Poincaré representation of heart rate variability.

6. The system of claim 3, wherein the third one of the subgroups comprises trigger factor descriptors selected from a group comprising:
   a ventricular trigeminy episode;
   a ventricular bigeminy episode;
   a ventricular tachycardia; or
   a supraventricular extrasystole.

7. An active medical device adapted to be implanted in a patient; the device comprising:
   at least one function;
   a neural network with at least two layers;
   a processor configured to:
      collect parameters relating to cardiac activity of the patient;
      for each of three subgroups of settings, extract three subgroups of descriptors from the collected parameters, wherein the three subgroups of settings correspond to classes of arrhythmogenic factors, a first one of the subgroups comprising electrophysiological substrate descriptors, a second one of the subgroups comprising pejorative modulator descriptors, and a third one of the subgroups comprising trigger factor descriptors;
      for each of the three subgroups of descriptors, classifying each descriptor based on an ability of the descriptor to label the patient and selecting a descriptor for each of the three subgroups of descriptors having a classification indicating the descriptor is relevant to the patient;
      evaluate the selected descriptors using the neural network with at least two layers, the at least two layers comprising:
         three neural sub-networks, each configured to process a different one of the selected descriptors wherein each neural sub-network generates an output; and
         at least one output neuron coupled to the three neural sub-networks and configured to generate an index of risk of ventricular arrhythmia based on the output of at least one of the three neural sub-networks; and
      compare the index of risk of ventricular arrhythmia to a threshold and activate or disable the at least one function of the active medical device in response to the index crossing the threshold.

8. The device of claim 7, wherein the function activated or disabled in response to the index crossing the threshold is at least one of:
   producing an alarm;
   activating or deactivating defibrillation shock therapies;
   activating new therapy zones;
   adjusting a sensitivity of an arrhythmia detector;
   activating or deactivating one or more algorithms; or
   modifying one or more therapy settings.

9. The device of claim 7, further comprising:
   a database of reference patients, storing for each reference patient:
      a plurality of descriptors developed from the parameters relating to the cardiac activity collected for the reference patient; and
      a marker indicating whether a ventricular arrhythmia was detected in the reference patient;
   wherein the active medical device is further configured to define a structure of the neural network by learning from the database of reference patients, wherein the active medical device is configured to, for each of the subgroups corresponding to arrhythmogenic factor classes:
      determine the structure of the neural sub-networks; and
      optimize the neural sub-network.

10. The device of claim 9, wherein the first one of the subgroups comprises electrophysiological substrate descriptors selected from a group comprising:
   a QRS residuum;
   a T-Wave residuum;
   a QRS-T angle;
   QTapex intervals;
   QTend intervals;
   a downslope of a T wave; or
   a ST segment elevation.

11. The device of claim 9, wherein the second one of the subgroups comprises pejorative modulator descriptors selected from a group comprising:
   a heart rate turbulence;
   a variability index between successive complexes;
   a standard deviation of normal range averages; or
   a Poincaré representation of heart rate variability.

12. The device of claim 9, wherein the third one of the subgroups comprises trigger factor descriptors selected from a group comprising:
   a ventricular trigeminy episode;
   a ventricular bigeminy episode;
   a ventricular tachycardia; or
   a supraventricular extrasystole.

13. A method comprising:
   collecting, by an active medical device, the active medical device performing at least one function and comprising a neural network with at least two layers and configured to be implanted in a patient, parameters relating to cardiac activity of the patient;
   for each of three subgroups of settings, extracting, by an active medical device, three subgroups of descriptors from the collected parameters, wherein the three subgroups of settings correspond to classes of arrhythmogenic factors, a first one of the subgroups comprising electrophysiological substrate descriptors, a second one of the subgroups comprising pejorative modulator descriptors, and a third one of the subgroups comprising trigger factor descriptors;
   for each of the three subgroups of descriptors, classifying each descriptor based on an ability of the descriptor to label the patient and selecting a descriptor for each of the three subgroups of descriptors having a classification indicating the descriptor is relevant to the patient;

evaluating, by the active medical device, the selected descriptors using the neural network with at least two layers, the at least two layers comprising:

three neural sub-networks, each configured to process a different one of the selected descriptors wherein each neural sub-network generates an output; and at least one output neuron coupled to the three neural sub-networks and configured to generate an index of risk of ventricular arrhythmia based on an output of at least one of the three neural sub-networks; and comparing the index of risk of ventricular arrhythmia to a threshold and activating or disabling the at least one function of the active medical device in response to the index crossing the threshold.

14. The method of claim 13, wherein the function activated or disabled in response to the index crossing the threshold is at least one of:

producing an alarm;
activating or deactivating defibrillation shock therapies;
activating new therapy zones;
adjusting a sensitivity of an arrhythmia detector;
activating or deactivating one or more algorithms; or
modifying one or more therapy settings.

15. The method of claim 13, further comprising:

in a database of reference patients, storing, for each reference patient:

a plurality of descriptors developed from the parameters relating to the cardiac activity collected for the reference patient; and a marker indicating whether a ventricular arrhythmia was detected in the reference patient; and defining a structure of the neural network by learning from the database of reference patients, wherein defining the structure of the neural network comprises, for each of the subgroups corresponding to arrhythmogenic factor classes:

determining the structure of the neural sub-networks; and optimizing the neural sub-network.

16. The method of claim 15, wherein the first one of the subgroups comprises electrophysiological substrate descriptors selected from a group comprising:

a QRS residuum;
a T-Wave residuum;
a QRS-T angle;
QTapex intervals;
QTend intervals;
a downslope of a T wave; or
a ST segment elevation.

17. The method of claim 15, wherein the second one of the subgroups comprises pejorative modulator descriptors selected from a group comprising:

a heart rate turbulence;
a variability index between successive complexes;
a standard deviation of normal range averages; or
a Poincaré representation of heart rate variability.

18. The method of claim 15, wherein the third one of the subgroups comprises trigger factor descriptors selected from a group comprising:

a ventricular trigeminy episode;
a ventricular bigeminy episode;
a ventricular tachycardia; or
a supraventricular extrasystole.

* * * * *